United States Patent [19]

Lambert et al.

[11] Patent Number: 4,614,834

[45] Date of Patent: Sep. 30, 1986

[54] DEHYDROCYCLIZATION WITH NONACIDIC L ZEOLITE

[75] Inventors: Susan L. Lambert, Rolling Meadows; Randy J. Lawson, Arlington Heights; Russell W. Johnson, Villa Park, all of Ill.; Jean-Pierre Gilson, Columbia, Md.

[73] Assignee: UOP Inc., Des Plaines, Ill.

[21] Appl. No.: 781,552

[22] Filed: Sep. 30, 1985

Related U.S. Application Data

[62] Division of Ser. No. 736,048, May 20, 1985.

[51] Int. Cl.$^4$ .............................................. C07C 2/52
[52] U.S. Cl. ...................................... 585/419; 502/66
[58] Field of Search ................................. 585/418, 419

[56] References Cited

U.S. PATENT DOCUMENTS

| | | | |
|---|---|---|---|
| 3,579,598 | 5/1971 | Hansford | 585/419 |
| 3,843,741 | 10/1974 | Yan | 208/137 X |
| 3,846,337 | 11/1974 | Young | 502/70 X |
| 3,886,094 | 5/1975 | Pilato et al. | 502/70 X |
| 4,247,726 | 1/1981 | Slaugh | 585/407 |
| 4,416,806 | 11/1983 | Bernard et al. | 502/74 |
| 4,430,200 | 2/1984 | Shihabi | 208/120 |
| 4,435,283 | 3/1984 | Buss et al. | 208/138 |
| 4,448,891 | 5/1984 | Cohen | 502/74 |
| 4,537,866 | 8/1985 | Gilson | 502/70 |
| 4,567,312 | 1/1986 | Miller et al. | 585/419 |

FOREIGN PATENT DOCUMENTS 2360540  9/1975  France ............................. 585/419

*Primary Examiner*—Brian E. Hearn
*Assistant Examiner*—O. Chaudhuri
*Attorney, Agent, or Firm*—Thomas K. McBride; John F. Spears, Jr.

[57] ABSTRACT

A novel catalyst composite is disclosed as well as a novel method of preparing the composite and a novel use for the composite. The novel composite comprises a nonacidic zeolite, catalytically effective amounts of a Group VIII metal component, and a silica support matrix derived by a high pH gelation of an alkali metal silicate sol. This novel composition has particular utility as a dehydrocyclization catalyst for the conversion of paraffins to aromatic compounds.

5 Claims, 2 Drawing Figures

DEHYDROCYCLIZATION WITH NONACIDIC L ZEOLITE

CROSS-REFERENCE TO RELATED APPLICATIONS

This application is a division of prior copending application, Ser. No. 736,048, filed May 20, 1985, the contents of which are incorporated herein by reference thereto.

BACKGROUND OF THE INVENTION

The present invention is directed toward a novel catalytic composite for the conversion of hydrocarbons and especially for effecting the dehydrocyclization of aliphatic hydrocarbons to aromatics. More particularly, the novel catalytic composite enables the conversion of $C_6$-plus paraffins to their corresponding aromatics with a high degree of selectivity thereby enabling the facile production of large quantities of aromatics.

In the past it has become the practice to effect conversion of aliphatic hydrocarbons to aromatics by means of the well-known catalytic reforming process. In catalytic reforming a hydrocarbonaceous feedstock, typically a petroleum naphtha fraction, is contacted with a Group VIII-containing catalytic composite to produce a product reformate of increased aromatics content. The naphtha fraction is typically a full boiling range fraction having an initial boiling point of from 50° to about 100° F. and an end boiling point of from about 325° to about 425° F. Such a full boiling range naphtha contains significant amounts of $C_6$-plus paraffinic hydrocarbons and $C_6$-plus naphthenic hydrocarbons. As is well known these paraffinic and naphthenic hydrocarbons are converted to aromatics by means of multifarious reaction mechanisms. These mechanisms include dehydrogenation, dehydrocyclization, isomerization followed by dehydrogenation. Naphthenic hydrocarbons are converted to aromatics by dehydrogenation. Paraffinic hydrocarbons may be converted to the desired aromatics by dehydrocyclization and may also undergo isomerization. Accordingly then, it is apparent that the number of reactions taking place in a catalytic reforming zone are numerous and, therefore, the typical reforming catalyst must be capable of effecting numerous reactions to be considered usable in a commercially feasible reaction system.

Because of the complexity and number of reaction mechanisms ongoing in catalytic reforming, it has become a recent practice to attempt to develop highly specific catalysts tailored to convert only specific reaction species to aromatics. Such catalysts offer advantages over the typical reforming catalyst which must be capable of taking part in numerous reaction mechanisms. In view of this, ongoing work has been directed toward producing a catalyst for the conversion of paraffinic hydrocarbons, particularly having six carbon atoms or more, to the corresponding aromatic hydrocarbon. Such a catalyst can be expected to be much more specific with respect to the final product compounds, resulting in fewer undesirable side reactions such as hydrocracking. As can be appreciated by those of ordinary skill in the art, increased production of aromatics is desirable. The increased aromatic content of gasolines, a result of lead phase down, as well as demands in the petrochemical industry make $C_6$-$C_8$ aromatics highly desirable products. It is, therefore, very advantageous to have a catalytic composition which is highly selective for the conversion of less valuable $C_6$-plus paraffins to the more valuable $C_6$-plus aromatics.

OBJECTS AND EMBODIMENTS

It is, therefore, a principal object of our invention to provide a catalytic composite, and a method of making and using the same for the conversion of hydrocarbons. A corollary objective is to provide a process for the conversion of $C_6$-plus paraffinic hydrocarbons, especially $C_6$-$C_8$ paraffinic hydrocarbons, to their corresponding aromatics.

Accordingly, a broad embodiment of the present invention is directed toward a catalytic composite comprising a nonacidic zeolite, catalytically effective amounts of a Group VIII metal component, and a silica support matrix derived by a high pH gelation of an alkali metal silicate sol.

An alternative broad embodiment of the present invention is a hydrocarbon conversion process characterized in that it comprises contacting at hydrocarbon conversion conditions, a hydrocarbon charge stock with a catalytic composite comprising a nonacidic zeolite, catalytically effective amounts of a Group VIII metal component, and a silica support matrix derived by a high pH gelation of an alkali metal silicate.

A further embodiment of the present invention comprises a method of preparing a catalytic composite comprising compositing a Group VIII metal component, a nonacidic zeolite, and a silica support matrix derived by a high pH gelation of an alkali metal silicate.

These as well as other objects and embodiments will become evident from the following, more detailed description of the present invention.

INFORMATION DISCLOSURE

Alumino silicates containing alkali metals are well known in the art. For example, U.S. Pat. No. 3,013,986, issued Dec. 19, 1968, discloses an alkali metal loaded L-zeolite. In particular this reference indicates that the potassium or the potassium/sodium form of the L-zeolite are the preferred starting materials for the alkali metal-loaded L-zeolite. The reference teaches that a dehydrated molecular sieve may be contacted with alkali metal vapors to produce an alkali metal-loaded molecular sieve wherein the alkali metal is contained within the interior of the zeolitic molecular sieve. The reference, however, does not disclose a catalytic composite comprising a nonacidic zeolite, catalytically effective amounts of Group VIII metal component, and a silica support matrix derived by a high pH gelation of an alkali metal silicate sol. Moreover, the reference does not disclose that such a composite would have any use as a hydrocarbon conversion catalyst.

U.S. Pat. No. 3,376,215, issued Apr. 2, 1968, discloses a hydrocarbon conversion catalyst comprising a cocatalytic solid support containing a Group VIII metal which support comprises (1) an adsorbent refractory inorganic oxide and (2) a mordenite structure zeolite having deposited thereon about 10 to about 1000 ppm by weight, based on zeolite, of a metal selected from the class of alkali metals, alkaline earth metals and mixtures thereof. This reference teaches that the support comprising a mordenite form zeolite and a refractory oxide be cocatalytic. The reference does teach that the cocatalytic refractory oxide may be a silica gel, or silica-alumina; however, the reference does emphasize that alumina is the preferred refractory oxide. Moreover, the only examples of refractory supports derived by gelation are alumina supports derived from alumina sols, well known to be acidic, with gelation being effected by neutralization with ammonia. Accordingly, this reference does not disclose the catalytic composite of the present invention. Firstly, the nonacidic zeolite of the present invention cannot be considered catalytic. Rather the nonacidic zeolite acts to modify the catalytic Group VIII metal component of the present invention and because the zeolite is in its nonacidic form it is noncatalytic. Secondly, there is no disclosure of use of a silica support matrix derived by a high pH gelation of an alkali metal silicate sol. The reference is completely silent as to the source of silica gel cocatalytic support disclosed therein. Nor is there disclosure of the surprising and unexpected results to be obtained by use of the composite of the instant invention.

U.S. Pat. No. 3,755,486, issued Aug. 28, 1973, discloses a process for dehydrocyclizing $C_6$–$C_{10}$ hydrocarbons having at least a $C_6$ backbone using an Li, Na, or K zeolite X or Y or faujasite impregnated with 0.3 to 1.4% platinum. This reference, however, fails to disclose the advantages to be derived by utilizing a catalytic composite comprising a nonacidic zeolite, a Group VIII metal component, and a silica support matrix derived by a high pH gelation of an alkali metal silicate. Likewise, U.S. Pat. No. 3,819,507, issued June 25, 1974, and U.S. Pat. No. 3,832,414, issued Aug. 27, 1974, while disclosing processes similar to that of U.S. Pat. No. 3,755,486 both fail to teach the use and advantages to be derived by such use of a catalyst in accordance with the invention.

U.S. Pat. No. 4,140,320, issued Aug. 1, 1978, discloses a process for dehydrocyclizing aliphatic hydrocarbons utilizing a type L-zeolite having exchangeable cations of which at least 90% are alkali metal ions selected from the group consisting of ions of sodium, lithium, potassium, rubidium and cesium and containing at least one metal selected from the group which consists of metals of Group VIII, tin, and germanium. This reference fails to disclose the catalytic composite of the present invention in that it does not disclose a bound catalyst system wherein the support matrix is derived by a high pH gelation of an alkali metal silicate sol. U.S. Pat. No. 4,417,083, issued Nov. 22, 1983, discloses a process for dehydrocyclization utilizing a substantially nonacidic zeolite having a pore diameter larger than 6.5Å and containing at least one metal selected from the group consisting of platinum, rhenium, iridium, tin and germanium. Additionally, the catalyst contains sulfur and alkaline cations. However, in this reference there is no disclosure of a catalyst having a silica support matrix wherein the matrix is derived from a high pH gelation of an alkali metal silicate sol.

U.S. Pat. No. 4,416,806, issued Nov. 22, 1983, discloses yet another paraffin dehydrocyclization catalyst comprising platinum, rhenium as a carbonyl, and sulfur on a zeolitic crystalline aluminosilicate compensated in more than 90% by alkaline cations and having a pore diameter of more than 6.5 Angstroms. This reference too fails to disclose a catalytic composition for dehydrocyclization in accordance with the invention. The reference does contain a broad disclosure of use of alumina or clay binders but does not disclose a binder even remotely like that of the invention.

Recent U.S. Pat. No. 4,430,200, issued Feb. 7, 1984, discloses a hydrocarbon conversion catalyst comprising a high silica zeolite such as mordenite or zeolite Y which has been base exchanged with an alkali metal. This reference does teach a silica support matrix but not one comparable to that of the invention which is derived by a high pH gelation of an alkali metal silicate sol. Moreover, the reference merely discloses the use of the prior art catalyst in a cracking process and not a dehydrocyclization process.

Recent U.S. Pat. No. 4,448,891, issued May 15, 1984, discloses a dehydrocyclization catalyst comprising an L-zeolite which has been soaked in an alkali solution having a pH of at least 11 for a time and at a temperature effective to increase the period of time over which the catalytic activity of the catalyst is maintained. Additionally, the catalyst contains a Group VIII metal. However, the reference fails to disclose use of a support matrix like that of the instant invention.

In summary then, the art has not recognized a catalytic composite for the conversion of hydrocarbons, especially the dehydrocyclization of $C_6$-plus paraffins to aromatics, comprising a nonacidic zeolite, catalytically effective amounts of a Group VIII metal component, and a silica support matrix derived by a high pH gelation of an alkali metal silicate sol. Moreover, the art has not recognized the attendant advantages to be derived from such a novel catalyst and use thereof.

DETAILED DESCRIPTION OF THE INVENTION

To reiterate briefly the present invention relates to a catalytic composite comprising a nonacidic zeolite, catalytically effective amounts of a Group VIII metal component, and a silica support matrix derived by a high pH gelation of an alkali metal silicate sol. Additionally, the invention has particular utility as a catalyst for the dehydrocyclization of $C_6$-plus paraffins, especially $C_6$–$C_{10}$ paraffins.

As heretofore indicated it is an essential feature of the catalyst of the present invention that it comprise a nonacidic zeolite. By "nonacidic zeolite" it is to be understood that it is meant that the zeolite has substantially all of its cationic sites of exchange occupied by nonhydrogen cationic species. Preferably, such cationic species will comprise the alkali metal cations although other cationic species may be present. Irrespective of the actual cationic species present in the sites of exchange, the nonacidic zeolite in the present invention has substantially all of the cationic sites occupied by nonhydrogen cations thereby rendering the zeolite substantially fully cationic exchanged and nonacidic. Many means are well known in the art for arriving at a substantially fully cationic exchanged zeolite and thus they need not be elaborated herein. The nonacidic zeolite of the present invention acts to modify the catalytic Group VIII metal and is substantially inert in the reaction. Hence, the nonacidic zeolite support of the present invention is noncatalytic and an essential feature of the present invention is that it be such.

Typical of the nonacidic zeolites which may be utilized in the present invention are X-zeolite, Y-zeolite and mordenite. Especially preferred in application of the present invention is L-zeolite. Of course, all of these zeolites must be in nonacidic form as defined above and, therefore, the cationic exchangeable sites are substantially fully cationic exchanged with nonhydrogen cationic species. As also indicated above, typically the cations occupying the cationic exchangeable sites will comprise one or more of the alkali metals including lithium, sodium, potassium, rubidium and cesium. Accordingly then, the nonacidic zeolite of the present invention may comprise the sodium forms of X-zeolite, Y-zeolite, or mordenite. An especially preferred nonacidic zeolite for application in the present invention is the potassium form of L-zeolite. It should also be understood, however, that the nonacidic zeolite of the invention may contain more than one type of the alkali metal cation at the cationic exchangeable sites, for example, sodium and potassium.

Irrespective of the particular nonacidic zeolite utilized, the catalyst of the present invention also comprises catalytically effective amounts of a Group VIII metal component, including catalytically effective amounts of nickel component, rhodium component, palladium component, iridium component, platinum component or mixtures thereof. Especially preferred among the Group VIII metal components is a platinum component. It is believed that in order for the Group VIII metal component to achieve greatest catalytic effectiveness it should be supported on the nonacidic zeolite as opposed to the silica support matrix. Accordingly, it is preferred that the Group VIII metal component be substantially supported on the nonacidic zeolite. The Group VIII metal component may be deposited on the nonacidic zeolite by any suitable means known in the art. For example, a platinum component may be impregnated into the nonacidic zeolite from an appropriate solution such as a dilute chloroplatinic acid solution and thereafter the nonacidic zeolite, having platinum supported thereon, may be bound in the silica support matrix. Alternatively, the Group VIII metal component may be deposited on the nonacidic zeolite by means of ion exchange in which case some of the cationic exchange sites of the nonacidic zeolite will contain Group VIII aetal cations. After ion exchange the Group VIII metal may be subject to a low temperature oxidation prior to any reduction step. Thereafter the nonacidic zeolite supporting the Group VIII metal component may be bound in the silica support matrix. As shall be explained more fully hereinafter the nonacidic zeolite may also first be bound in the silica support matrix and thereafter the Group VIII metal component may be selectively composited with the zeolite and support matrix, preferably in any manner which will result in the selective deposition of the Group VIII metal component on the nonacidic zeolite.

Irrespective of the exact method of depositing the Group VIII metal component, any catalytically effective amount of Group VIII metal component may be employed. The optimum Group VIII metal component content will depend generally on which Group VIII metal component is utilized in the catalyst of the invention. However, generally from about 0.01 to about 5.0 wt. % of the Group VIII metal component based on the weight of the zeolite, Group VIII metal component, and silica support matrix may be advantageously deposited on the zeolite.

It should further be understood that best results are achieved when the Group VIII metal component is highly dispersed on the nonacidic zeolite. The Group VIII metal component is most effective in a reduced state. Any suitable means may be employed for reducing the Group VIII metal component and many are well known in the art. For example, after deposition on the nonacidic zeolite the Group VIII metal component may be subjected to contact with a suitable reducing agent, such as hydrogen, at an elevated temperature for a period of time.

In addition to comprising a Group VIII metal component it is contemplated in the present invention, that the catalyst thereof may contain other metal components well known to have catalyst modifying properties. Such metal components include components of rhenium, tin, cobalt, indium, gallium, lead, zinc, uranium, thallium, dysprosium, and germanium, etc. Incorporation of such metal components have proven beneficial in catalytic reforming as promoters and/or extenders. Accordingly, it is within the scope of the present invention that catalytically effective amounts of such modifiers may be beneficially incorporated into the catalyst of the present invention improving its performance.

Irrespective of the particular Group VIII metal component and catalytic modifiers composited with the catalytic composition of the present invention, a further essential feature of the invention is a silica support matrix derived from a high pH gelation of an alkali metal silicate sol. Silica support matrices are well known in the art. Such support matrices have found wide use in the petroleum and petrochemical industries. In particular, they have been used to bind molecular sieves for numerous separation and catalytic processes. However, as will be further explained hereinafter the silica support matrix of the present invention, being derived from a high pH gelation of an alkali metal silicate sol, results in surprising and unexpected benefits in the present invention.

As is well known in the art the use of a silica support matrix may enhance the physical strength of a catalyst. Accordingly, by binding the nonacidic zeolite in the silica support matrix a catalyst of enhanced physical strength may be obtained. Additionally, binding the nonacidic zeolite allows formation of shapes suitable for use in catalytic conversion processes. For example, by use of the silica support the catalyst of the instant invention may be formulated into spheres. The use of spheres is well known to be advantageous in various applications. In particular, when the catalyst of the instant invention is emplaced within a continuously moving bed system, a spherical shape enhances the ability of the catalyst to move easily through the reaction zones. Of course, other shapes may be employed where advantageous. Accordingly, the catalyst of the instant invention may be formed into the shape of an extrudate, saddle, etc. Irrespective of the particular shape of the silica support matrix, sufficient nonacidic zeolite and silica support matrix should be employed in the catalyst of the invention such that the catalytic composition comprises from about 25 to 75 wt. % nonacidic zeolite based on the weight of the zeolite and support matrix. A composite comprising about 50 wt. % nonacidic zeolite based on the weight of the zeolite and support matrix is preferred. Additionally the nonacidic zeolite crystallites should be evenly distributed throughout the silica support matrix. Such uniform distribution of the nonacidic zeolite imparts improved particle strength characteristics and reaction properties to the catalytic composite.

Another essential feature of the present invention is that the silica support matrix be derived from a high pH gelation of an alkali metal silicate sol. It is to be understood that as used therein the term high pH gelation means that said gelation is effected at a pH of 7 or more. This high pH gelation results in two distinct benefits. First the high pH gelation allows incorporation of the nonacidic zeolite into the alkali metal silicate sol prior to gelling the support matrix without fear of loss of crystallinity. As is known zeolites tend to be sensitive to the pH of their environment. Accordingly, zeolites dispersed in an acidified sol may lose crystallinity during gelation. This disadvantage is overcome by the high pH gelation utilized in the invention to derive the silica support matrix. Since a most facile means of preparing the catalyst of the present invention is to disperse the nonacidic zeolite in an alkali metal silicate sol prior to gelation, the high pH environment of the gelation avoids the attendant possibility of loss of zeolite in the preparation of the catalytic composite of the invention. The high pH gelation also avoids the introduction of acid sites into the nonacidic zeolite. Introduction of such sites would cause the zeolite to promote undesirable side reactions such as cracking, etc.

The second advantage of deriving the silica support matrix from a high pH gelation of an alkali metal silicate sol is that it results in a finished catalytic composite having surprising and unexpected selectivity for the production of aromatic hydrocarbons from $C_6$-plus paraffins. Although it is not fully understood, it is believed that the high pH gelation of the soluble alkali metal silicate results in a silica support matrix with increased interaction between the nonacidic zeolite and the silica of the support matrix. This interaction apparently results in a modification of the Group VIII metal component such that the overall selectivity of the catalyst for the production of aromatics from $C_6$-plus paraffins is enhanced. Accordingly then, deriving the silica support matrix from the high pH gelation of an alkali metal silicate not only allows facile preparation of the final catalytic composite but also results in a catalytic composite of surprisingly high selectivity for the production of $C_6$-plus aromatics.

As is well known in the art, alkali metal silicate sols may be used as precursors for silica support matrices. Waterglass (sodium silicate) has often been used as a precursor for support matrices. Additionally, there are various means known for effecting high pH qelation. However, the preferred alkali metal silicate and high pH gelation technique is that set forth in U.S. Pat. No. 4,537,866 the contents of which have been incorporated herein. In this preferred method a lithium silicate sol is caused to gel by heating the sol to a temperature of about 70° C. or more. Thereafter, the gelled lithium silicate sol is subjected to a washing step to remove lithium therefrom thereby causing the gel to set. The lithium silicate sols employable in the present invention will have $SiO_2/Li_2O$ molar ratios of up to about 25. Especially preferred lithium silicates are those having $SiO_2/Li_2O$ molar ratios of from about 4 to about 8. These lithium silicate sols will all have a pH in excess of about 7 with the preferred lithium silicate sols having a pH of from about 10 to about 11. Since the lithium silicate sols may be gelled by heating without the need of adjusting the pH with a gelling agent (typically an acid), it is possible to effect a high pH gelation as defined herein. Accordingly then, in making the catalytic composite of the present invention by the method set forth in previously referred to U.S. Pat. No. 4,537,866 the nonacidic zeolite is dispersed in the lithium silicate sol. Shaped particles of the lithium silicate sol are thereafter forced. The shaped particles are then heated to a temperature in excess of about 70° C. thereby causing the shaped particles to form gels. Thereafter, the lithium silicate gels containing nonacidic zeolite are subjected to a washing step to remove lithium therefrom. This washing step causes the gels to set.

As will be recognized by those having ordinary skill in the art, many methods may be employed in forming the shaped particles of nonacidic zeolite containing lithium silicate sol. These include extrusion, pilling, molding, etc. Of all the many well known methods, the particularly preferred method of forming the shaped particles of the present invention is the oil-drop method. In the oil-drop method particles of sol are formed as droplets. Typically, these droplets are formed by passing the sol through suitable orifices or from a rotating disc. The droplets then fall into a suspending medium typically oil. As the droplets pass through the oil suspending medium they take on a spheroidal form. The diameter of the spheroidal particles may be controlled by adjusting the diameter of the orifices from which the droplets flow and/or the vibrational rate of the dropping head. As the nonacidic zeolite containing sol droplets pass through the suspending medium, they are heated to a temperature of about 70° C. or more thereby causing the sol to gel. The gelled particles are then collected, aged and subjected to a washing step to remove lithium therefrom. Accordingly then, there results a nonacidic zeolite bound within a silica support matrix derived by a high pH gelation of an alkali metal silicate with the preferred alkali metal silicate being lithium silicate.

As heretofore indicated, it is preferred that the nonacidic zeolite be composited with the silica support matrix and thereafter be composited with the Group VIII metal component. Moreover, as was indicated, it is preferred that the Group VIII metal component be supported substantially on the nonacidic zeolite. Of course, any suitable means of achieving these preferred steps may be utilized in the invention. However, a particularly preferred method is the use of a selective ion exchange procedure whereby the Group VIII metal component is deposited substantially on the nonacidic zeolite as opposed to the silica support matrix.

The selective deposition of platinum on the nonacidic zeolite as opposed to the silica support matrix may be achieved by controlling the pH of the exchange solution at a value less than 8. The silica support matrix is known to be a cation exchanger at a pH greater than about 8. By way of contrast the zeolite ion exchange capacity is not pH dependent. Thus, when the Group VIII metal component is to be deposited by means of ion exchange with an ion exchange solution having a pH of greater than about 8, there will be a tendency for the Group VIII metal component to be deposited both on the silica support matrix and the nonacidic zeolite. However, at pH values of less than 8 the silica support matrix loses its cation exchange potential. Thus, by utilizing a cation exchange solution having a pH of less than about 8, will result in the Group VIII metal component being deposited substantially selectively on the nonacidic zeolite alone. It is particularly preferred that the pH of the cation exchange solution be maintained at a pH in the range of from about 4 to about 8. This will result in the selective deposition of the Group VIII metal component on the nonacidic zeolite as opposed to the silica support matrix.

Irrespective of its exact method of preparation, the catalytic composition of the present invention has particular utility as a hydrocarbon conversion catalyst. Accordingly, a hydrocarbon charge stock is contacted at hydrocarbon conversion conditions with the catalytic composite of the present invention. A wide range of hydrocarbon conversion conditions may be employed and will depend upon the particular charge stock and reaction to be effected. Generally, these conditions include a temperature of about 32° to about 1500° F., a pressure of from atmospheric to about 100 atmospheres, a liquid hourly space velocity (calculated on the basis of equivalent liquid volume of the charge stock contacted with the catalyst per hour divided by the volume of conversion zone containing catalyst) of about 0.2 hr.$^{-1}$ to 15 hr.$^{-1}$. Furthermore, hydrocarbon conversion conditions may include the presence of a diluent such as hydrogen. When such is the case the hydrogen to hydrocarbon mole ratio may be from about 0.5:1 to about 30:1.

A particularly preferred application of the catalyst of the present invention is its use as a dehydrocyclization catalyst and in particular for the dehydrocyclization of $C_6$–$C_8$ nonaromatic hydrocarbons. Accordingly, a hydrocarbon charge stock comprising $C_6$–$C_8$ nonaromatic hydrocarbons is contacted with the catalyst of the present invention at dehydrocyclization conditions. Dehydrocyclization conditions include a pressure of from about 0 psig to about 1000 psig, with the preferred pressure being from about 0 psig to about 600 psig, a temperature of from about 800° to about 1200° F., and a liquid hourly space velocity of from about 0.1 hr.$^{-1}$ to about 10 hr.$^{-1}$. Preferably, hydrogen may be employed as a diluent. When present, hydrogen may be circulated at a rate of from about 0.1 to about 10 moles of hydrogen per mole of hydrocarbon.

According to the present invention a hydrocarbon charge stock is contacted with the catalyst of the present invention in a hydrocarbon conversion zone. This contacting may be accomplished by using the catalyst in a fixed-bed system, a moving-bed system, a fluidized-bed system, or in a batch-type operation. The hydrocarbon charge stock and, if desired, a hydrogen-rich gas as diluent are typically preheated by any suitable heating means to the desired reaction temperature and then are passed into a conversion zone containing the catalyst of the invention. It is, of course, understood that the conversion zone may be one or more separate reactors with suitable means therebetween to ensure that the desired conversion temperature is maintained at the entrance to each reactor. It is also important to know that the reactants may be contacted with the catalyst bed in either upward, downward, or radialflow fashion with the latter being preferred. In addition the reactants may be in the liquid phase, a mixed liquid-vapor phase, or a vapor phase when they contact the catalyst. Best results are obtained when the reactants are in the vapor phase.

In the case where the catalyst of the present invention is employed in a dehydrocyclization process, the dehydrocyclization system will comprise a reaction zone containing the catalyst of the present invention. As indicated heretofore, the catalyst may be utlized within the reaction zone as a fixed-bed system, a moving-bed system, a fluidized-bed system, or in a batch-type operation; however, in view of the operational advantages well recognized in the art it is preferred to utilize the catalyst of the present invention in a moving-bed system. In such a system the reaction zone may be one or more separate reactors with heating means therebetween to compensate for the endothermic nature of the dehydrocyclization reaction that takes place in each catalyst bed. The hydrocarbon feedstream, preferably comprising $C_6$–$C_8$ nonaromatic hydrocarbons, is charged to the reaction zone as a continuous moving bed. Therein it is contacted with the hydrocarbon charge stock to effect the dehydrocyclization thereof.

After contact with the catalyst of the present invention the hydrocarbon charge stock having undergone dehydrocyclization is withdrawn as an effluent stream from the reaction zone and passed through a cooling means to a separation zone. In the separation zone the effluent may be separated into various constituents depending upon the desired products. When hydrogen is utilized as a diluent in the reaction zone the separation zone will typically comprise a vapor-liquid equilibrium separation zone and a fractionation zone. A hydrogen-rich gas is separated from a high octane liquid product containing aromatics generated within the dehydrocyclization zone. After separation at least a portion of the hydrogen-rich gas may be recycled back to the reaction zone as diluent. The balance of the hydrogen-rich gas may be recovered for use elsewhere. The high octane liquid product comprising aromatics may then be passed to a fractionation zone to separate aromatics from the unconverted constituents of the charge stock. These unconverted constituents may then be passed back to the reaction zone for processing or to other processes for utilization elsewhere.

A wide range of hydrocarbon charge stocks may be employed in the process of the present invention. The exact charge stock utilized will, of course, depend on the precise use of the catalyst. Typically, hydrocarbon charge stocks which may be used in the present invention will contain naphthenes and paraffins, although in some cases aromatics and olefins may be present. Accordingly, the class of charge stocks which may be utilized includes straight-run naphthas, natural naphthas, synthetic naphthas, and the like. Alternatively, straight-run and cracked naphthas may also be used to advantage. The naphtha charge stock may be a full-boiling range naphtha having an initial boiling point of from about 50° to about 150° F. and an end boiling point within the range of from about 325° F. to 425° F., or may be a selected fraction thereof. It is preferred that the charge stocks employed in the present invention be treated by conventional catalytic pretreatment methods such as hydrorefining, hydrotreating, hydrodesulfurization, etc., to remove substantially all sulfurous, nitrogenous and water-yielding contaminants therefrom.

When the catalyst of the present invention is utilized as a dehydrocyclization catalyst it is preferred that the charge stock substantially comprise paraffins. This, of course, is a result of the fact that the purpose of a dehydrocyclization process is to convert paraffins to aromatics. Because of the value of $C_6$–$C_8$ aromatics it is additionally preferred that the hydrocarbon charge stock comprise $C_6$–$C_8$ paraffins. However, notwithstanding this preference the hydrocarbon charge stock may comprise naphthenes, aromatics, and olefins in addition to $C_6$–$C_8$ paraffins.

In order to more fully demonstrate the attendant advantages arising from the present invention the following examples are set forth. It is to be understood that the following is by way of example only and is not intended as an undue limitation on the otherwise broad scope of the present invention.

It should be understood that there are three parameters useful in evaluating hydrocarbon conversion catalyst performance, and in particular in evaluating and comparing dehydrocyclization catalysts. The first is "activity" which is a measure of the catalyst's ability to convert reactants at a specified set of reaction conditions. The second catalyst performance criteria is "selectivity" which is an indication of the catalyst's ability to produce a high yield of the desired product. The third parameter is "stability" which is a measure of the catalyst's ability to maintain its activity and selectivity over time. In the appended examples the criteria which will be of interest is catalyst selectivity. For purposes of the following, the catalyst of the invention is exemplified as a dehydrocyclization catalyst and the measure of catalyst selectivity is the conversion of the paraffin reactants to aromatics.

BRIEF DESCRIPTION OF THE DRAWINGS

In FIG. 1 the performance data for two catalysts are depicted therein, Catalyst A, not of the invention, and Catalyst B, not of the invention. FIG. 2 contains the results of testing Catalyst C of the invention and Catalyst D, not of the invention.

EXAMPLE I

A first catalyst comprising a silica-bound nonacidic zeolite was prepared. However, in this instance the silica support matrix was not derived from a high pH gelation procedure. For this catalyst the nonacidic zeolite comprised a potassium exchanged L-zeolite. The catalyst was prepared by admixing L-zeolite and a colloidal silica sol in such quantities that the finished composite comprised 10 wt. % silica and 90 wt. % L-zeolite based on the weight of the silica and L-zeolite. The mixture was evaporated to dryness, ground, and extruded using about 5% polyvinyl alcohol as an extrusion aid. The extrudates were then calcined at 500° C. The calcined extrudates were then subjected to ion exchange step in order to deposit platinum thereon. An ion exchange solution comprising $Pt(NH_3)_4Cl_2/KCl$ was utilized. Thereafter the extrudates were subjected to an oxidation and reduction step at 350° C. The finished catalyst comprised 0.877 wt. % platinum. This catalyst was designated Catalyst A. Although bound in a support matrix comprising silica, because the support matrix of Catalyst A was not derived by a high pH gelation of an alkali metal silicate procedure, Catalyst A was not in accordance with the invention.

EXAMPLE II

A second catalyst was prepared in this example. This catalyst comprised an unbound L-zeolite in potassium form. The unbound L-zeolite was subjected to an ion exchange step substantially as set forth in Example I in order to deposit a platinum component thereon. After deposition of the platinum component the unbound L-zeolite was given an oxidation treatment in air at about 350° C. and thereafter a reduction step in hydrogen at about 350° C. The finished catalyst contained 0.657 wt. % platinum. This catalyst was designated Catalyst B and was not in accordance with the invention.

EXAMPLE III

In this example Catalysts A and B were subjected to a test procedure to determine their relative performance as dehydrocyclization catalysts. The tests were conducted in a pilot plant comprising a reaction zone in which the catalyst to be tested was emplaced. The conditions within the reaction zone were a pressure of 100 psig, a 1.0 hr.$^{-1}$ liquid hourly space velocity, and a 500° C. reaction inlet temperature. Sufficient hydrogen was admixed with the charge stock prior to contact with the catalyst to produce a hydrogen to hydrocarbon molar ratio of 10.0:1.0. The feedstock was a blend of iso $C_6$+iso $C_7$+normal $C_6$+normal $C_7$ paraffins with a small amount of alkylcyclopentanes.

Figure 1:
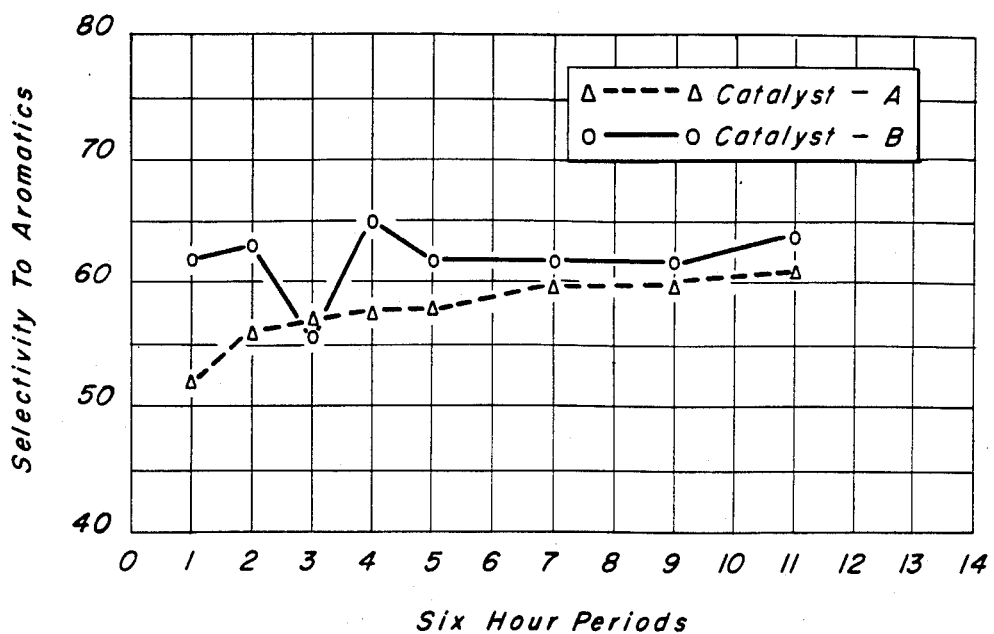
FIGS. 1 and 2 are plots of catalyst selectivity for the production of aromatics as a function of time.

The hydrocarbon feedstock was contacted with the catalyst emplaced within the reaction zone and the reaction zone effluent was analyzed. The results of the data collected in testing both Catalysts A and B in this test are set forth in FIG. 1. FIG. 1 is a graphical representation of the catalyst selectivity for the production of aromatics as a function of time measured in periods of 6 hours. For the purposes of this example, selectivity is defined as the grams of aromatics produced per gram of feed converted, multiplied by 100. As can be seen from FIG. 1, Catalyst B with the exception of Period 3 exhibited higher selectivities for the production of aromatics than did Catalyst A. Accordingly, the unbound L-zeolite containing a platinum component supported thereon exhibited better selectivity for the production of aromatics than did a catalyst comprising a platinum component, an L-zeolite bound within a silica support matrix.

EXAMPLE IV

In this example a catalyst was made in accordance with the invention. About 300 g of L-zeolite in potassium form was ball-milled for about 2 hours with 1382 g of a lithium silicate sol in which the $SiO_2/Li_2O$ was 6 and the pH of the sol was about 10.5. The sol was then dispersed as droplets into an oil suspending medium. Therein the sol droplets were gelled at a temperature of about 100° C. The gel spheres were then aged in the oil for about 2 hours at a temperature in the range of from about 100° to 150° C. and a pressure of about 80 psig. Thereafter the aged spheres were washed with 14 liters of 0.15 molar KCl solution at about 95° C. for 2 hours to remove lithium therefrom. The spheres were then dried at 95° C. After drying the spheres were gradually heated over a 6 hour period to 610° C. The spheres were then calcined in dry air for 2 hours at 610° C. The resulting spheres comprised a potassium form L-zeolite bound in a silica support matrix derived from a high pH gelation of an alkali metal silicate sol. The composition was 50 wt. % L-zeolite and 50 wt. % silica.

The calcined spheres were then subjected to an ion exchange step in order to deposit a platinum component substantially on the L-zeolite. The ion exchange solution comprised a 0.030 molar $Pt(NH_3)_4Cl_2$/0.90 molar KCl solution maintained at a pH below 8. As indicated heretofore by maintaining the pH below 8, it is possible to deposit substantially all of the platinum on the L-zeolite. The catalyst was then water washed and dried at a temperature of about 95° C. After drying the catalyst was oxidized at a temperature of 350° C. and reduced in a hydrogen stream at a temperature of about 350° C. The resulting catalyst comprised 0.786 wt. % platinum. This catalyst, in accordance with the invention, was designated Catalyst C.

EXAMPLE V

An unbound nonacidic zeolite catalyst was prepared substantially as set forth in Example II above. In this example, however, the catalyst contained about 0.882 wt. % platinum on a potassium form L-zeolite. Accordingly, the catalyst was substantially the same as Catalyst B of Example II; however, the catalyst in this example contained more platinum component. The catalyst made in this example was designated Catalyst D.

EXAMPLE VI

In order to determine the relative performance as dehydrocyclization catalysts of a catalyst made in accordance with the invention and a catalyst comprising an unbound L-zeolite containing platinum, Catalysts C and D were subjected to a test. The test was carried out in a pilot plant substantially the same as that utilized to test Catalysts A and B in Example III above. However, in this instance a different testing procedure was utilized. The conditions employed during this test of Catalysts C and D were a reaction zone inlet temperature of 500° C., a 1.0 hr.$^{-1}$ liquid hourly space velocity, and a reaction zone pressure of 50 psig. Hydrogen was admixed with the hydrocarbon charge stock prior to contact with the catalysts. Sufficient hydrogen on a once through basis was used to provide a 5:1 ratio of moles of hydrogen to moles of hydrocarbon charge stock. The procedure followed in testing was to first contact the catalyst with charge stock at a reaction zone temperature of 410° C. The 410° C. reaction zone inlet temperature was maintained for a period of 7 hours. Thereafter the reaction zone inlet temperature was increased to 500° C. over a 3 hour period. The 500° C. temperature was then maintained over a 12 hour test interval during which the reaction zone effluent was analyzed by the on-line gas chromatograph each hour.

The charge stock utilized in this example had the following analysis:

| | |
|---|---|
| $C_3/C_4/C_5$ paraffins | 0.4 wt. % |
| $C_6$ paraffins | 69.5 wt. % |
| $C_6$ naphthenes | 0.7 wt. % |
| $C_7$ paraffins | 21.4 wt. % |
| $C_7$ naphthenes | 8.0 wt. % |
| Total | 100.0 wt. % |

Figure 2:
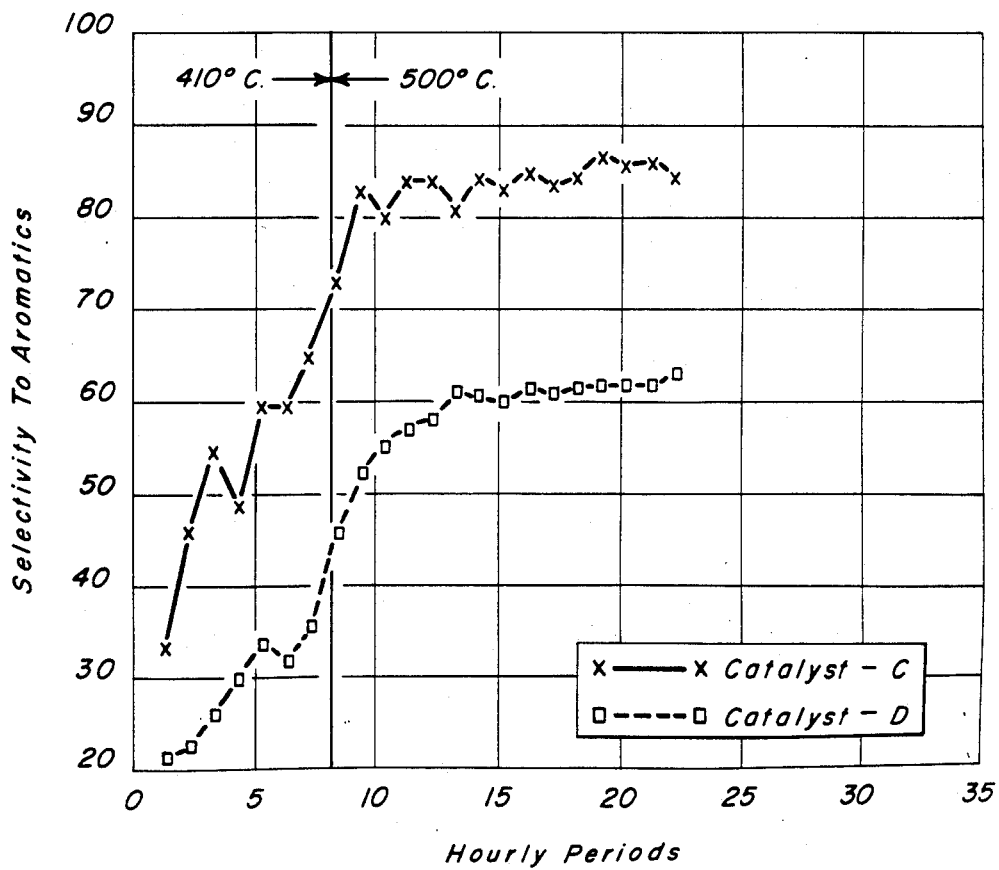

The results from the test are set forth in FIG. 2. For purposes of FIG. 2 in the following discussion, selectivity has the same definition as that given in Example III above. Surprisingly and unexpectedly, it can be seen from the data in FIG. 2 that the catalyst of the invention exhibited a much higher selectivity for the production of aromatics than did the unbound L-zeolite and platinum catalyst. As will be noted from the data in FIG. 1, this is contrary to the result observed in Example III above. In Example III above the unbound L-zeolite and platinum catalyst performed better than the silica bound, L-zeolite and platinum catalyst. However, in this example the silica bound L-zeolite and platinum catalyst exhibited higher selectivity for the production of aromatics than did the unbound L-zeolite and platinum catalyst. It can, therefore, be concluded that the surprising and unexpected results achieved by means of the invention result from the fact that the silica support matrix of Catalyst C was derived by a high pH gelation of an alkali netal silicate sol. Catalyst A, a silica bound L-zeolite catalyst containing platinum, did not exhibit superior selectivity in comparison to unbound L-zeolite catalyst containing platinum. The difference in the relative selectivities exhibited in this example and in Example III cannot be attributed to the varying platinum levels in that in each case the unbound catalyst contained more platinum on a weight percent basis than did the bound catalyst. As indicated heretofore, the nonacidic zeolite is noncatalytic and merely acts to modify the Group VIII metal component which is the catalytic element in the system.

Although it is not fully understood why binding the platinum containing nonacidic zeolite in a silica support matrix derived from a high pH gelation of an alkali metal silicate sol results in improved selectivity, it is believed that interaction resulting from the high pH gelation conditions between the silica of the support matrix and the zeolite further modifies the platinum component catalytic function. This further modification results in an improved selectivity for the conversion of paraffins to aromatic compounds.

What is claimed is:

1. A dehydrocyclization process comprising contacting $C_6$–$C_{10}$ aliphatic hydrocarbons at a pressure of from about 0 psig to about 600 psig, a temperature of from about 800° F. to about 1200° F., a liquid hourly space velocity of from about 0.1 hr$^{-1}$ to about 10 hr$^{-1}$ and a molar ratio of hydrogen to said hydrocarbons of from about 0.1 to about 10 with a catalyst composite comprising nonacidic L zeolite, a catalytically effective amount of Group VIII metal component, and a silica support matrix, said catalytic composite being produced by the method comprising admixing said nonacidic L zeolite with an alkali metal silicate sol, causing the zeolite-containing sol to gel while maintaining the pH of the sol while in contact with the zeolite at a value of at least 7, recovering the resulting catalytic composite, and incorporating a catalytically effective amount of a Group VIII metal in said catalytic composite.

2. The process of claim 1 further characterized in that the support matrix is derived from a high pH gelation of a lithium silicate sol.

3. The process of claim 1 further characterized in that the catalytic composite comprises from about 25 to 75 wt. % nonacidic zeolite based on the weight of the zeolite and support matrix.

4. The process of claim 1 further characterized in that the Group VIII metal component comprises a platinum component.

5. The process of claim 1 further characterized in that the catalytic composite comprises from about 0.01 to about 5.0 wt. % of the Group VIII metal component based on the weight of the zeolite, support matrix, and Group VIII metal component.

* * * * *